(12) United States Patent
Bourne

(10) Patent No.: US 8,681,936 B2
(45) Date of Patent: Mar. 25, 2014

(54) RADIOTHERAPEUTIC APPARATUS

(75) Inventor: Duncan Neil Bourne, Redhill (GB)

(73) Assignee: Elekta AB (Publ), Stockholm (SE)

( * ) Notice: Subject to any disclaimer, the term of this patent is extended or adjusted under 35 U.S.C. 154(b) by 1021 days.

(21) Appl. No.: 12/514,125

(22) PCT Filed: Nov. 10, 2006

(86) PCT No.: PCT/EP2006/010778
§ 371 (c)(1),
(2), (4) Date: May 8, 2009

(87) PCT Pub. No.: WO2008/055531
PCT Pub. Date: May 15, 2008

(65) Prior Publication Data
US 2010/0057061 A1    Mar. 4, 2010

(51) Int. Cl.
*A61N 5/10* (2006.01)
*H05G 1/64* (2006.01)
*G21K 1/02* (2006.01)
*G21K 1/04* (2006.01)
*A61N 5/06* (2006.01)

(52) U.S. Cl.
USPC .............. 378/65; 378/147; 378/152; 378/98; 607/88

(58) Field of Classification Search
USPC ........ 606/9–21; 378/145–161, 65, 98; 607/88
See application file for complete search history.

(56) References Cited

U.S. PATENT DOCUMENTS

| | | | | |
|---|---|---|---|---|
| 4,882,741 A | * | 11/1989 | Brown | 378/152 |
| 5,012,506 A | * | 4/1991 | Span et al. | 378/152 |
| 5,438,991 A | | 8/1995 | Yu et al. | |
| 6,108,399 A | * | 8/2000 | Hernandez-Guerra et al. | 378/65 |
| 2004/0013237 A1 | * | 1/2004 | Brown et al. | 378/147 |
| 2004/0234031 A1 | * | 11/2004 | Francke et al. | 378/98 |

FOREIGN PATENT DOCUMENTS

| | | |
|---|---|---|
| EP | 0314231 A2 | 5/1989 |
| GB | 2035769 A | 6/1980 |

OTHER PUBLICATIONS

PCT International Search Report, Jul. 20, 2007.
PCT Written Opinion of the International Searching Authority.

* cited by examiner

*Primary Examiner* — Ahmed Farah
*Assistant Examiner* — William Cheng
(74) *Attorney, Agent, or Firm* — Westman, Champlin & Koehler, P.A.; Z. Peter Sawicki

(57) ABSTRACT

A radiotherapeutic apparatus comprises a source of therapeutic radiation, a source of visible light arranged to cast a light field corresponding to the beam of radiation, and a multileaf collimator for shaping the beams, wherein a filter is disposed in the path of the visible light beam having a plurality of linear dark sections corresponding to leaves of the collimator. This prevents the incident light from falling on the leaves and removes the ghost images at source. By placing the filter in the head, the line can be very narrow and will be blurred into penumbra at the isocentre. This is therefore a very inexpensive yet effective method of reducing ghosting. A mirror can deflect the path of the visible light to correspond to that of the radiation beam, and the filter can be disposed anywhere in the beam path, such as prior to the mirror, subsequent to the mirror and prior to the collimator, or subsequent to the collimator. The filter thus creates dark sections in the light field corresponding to leaves (preferably all the leaves) of the collimator.

8 Claims, 4 Drawing Sheets

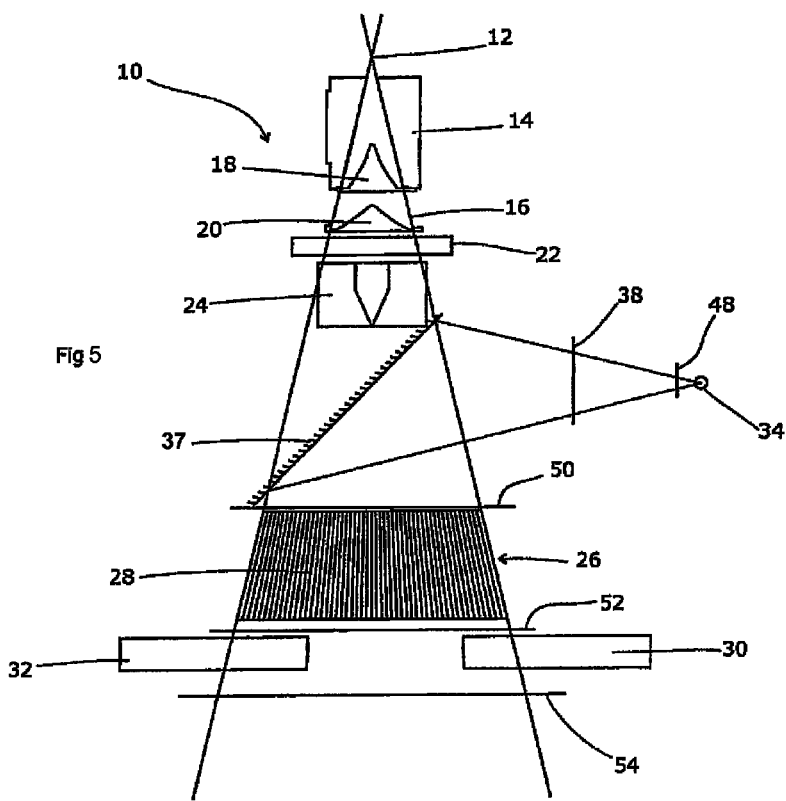

RADIOTHERAPEUTIC APPARATUS

CROSS-REFERENCE TO RELATED APPLICATION

This Application is a Section 371 National Stage Application of International Application No. PCT/EP2006/010778, filed Nov. 10, 2006 and published as WO 2008/055531 A1 on May 15, 2008, the content of which is hereby incorporated by reference in its entirety.

BACKGROUND OF THE INVENTION

Radiotherapy works by directing a beam of harmful radiation towards the site of (for example) a tumour. The radiation inflicts damage on the tumour and causes its reduction. In order to prevent collateral damage to the healthy tissues surrounding the tumour, the beam will be shaped to reduce the dose applied outside the tumour, for example by conforming to the outside shape of the tumour. It will also (generally) be directed towards the tumour from a variety of different directions along axes that are centred on the tumour. Thus, by rotating the source around the patient and varying the shape of the tumour, a three-dimensional dose distribution can be built up which is at a maximum within the tumour and is minimised elsewhere.

It is therefore important to ensure that the patient is correctly positioned within the apparatus. The apparatus will work to its own set of co-ordinate axes and will expect the tumour to be positioned in the correct location at its "isocentre", the point in space about which the radiation source rotates and which is therefore always on the radiation axis. Fine control of the patient position can be achieved by providing an articulated couch for the patient, and modern couches are able to perform adjustments to the patient position in all six degrees of freedom. This is controlled in response to data obtained from a diagnostic x-ray source integrated with the radiotherapeutic apparatus, which can provide real time information as to the current position of the patient.

However, it is necessary to ensure that the patient position is approximately correct before such apparatus can be used to fine-tune the position of the patient. The initial positioning of the patient to an accuracy of a few millimeters is therefore assisted by providing a light source within the apparatus, together with one or more mirrors (as necessary) to direct the light beam along the path of the radiation. Cross-hairs within the beam path can be used to align the patient, and the light field can be used to check operation of the various collimators that are provided in order to limit the shape of the radiation beam.

One such collimator is the so-called "multi-leaf collimator" (MLC), as shown (for example) in EP-A-0,314,214. This consists of a plurality of leaves that can be moved into and out of the radiation path; each leaf has a sufficient depth along the radiation axis to absorb the incident radiation, and a narrow width transverse to the radiation axis. A large number of such leaves are placed alongside each other in two opposing banks, and each can be moved independently so that they can (collectively) define an arbitrary edge to the radiation field.

One difficulty that can arise when the MLC is being tested with the optical light source is that the significant depth of the leaves along the beam axis and at a very shallow angle thereto allows them to reflect the incident light. Where a particular leaf is extended or withdrawn significantly beyond its adjacent leaves, such reflective surfaces are created in the beam path and lead to the phenomenon of "ghosting", whereby a spurious bright line is created in the field. Previous efforts to eliminate ghosting have relied on surface treatment of the leaves to reduce their reflective properties, but the very shallow angle at which they are presented to the light source makes this difficult.

SUMMARY OF THE INVENTION

The present invention therefore provides a radiotherapeutic apparatus comprising a source of therapeutic radiation, a source of visible light arranged to cast a light field corresponding to the beam of radiation, and a muitileaf collimator for shaping the beams, wherein a filter is disposed in the path of the visible light beam, having a plurality of linear dark sections corresponding to leaves of the collimator.

A mirror can deflect the path of the visible light to correspond to that of the radiation beam. This allows the visible light source to be disposed out of the radiation beam, and for the source of visible light to be disposed in substantially the same optical location as the source of therapeutic radiation.

The filter can be disposed anywhere in the beam path, such as prior to the mirror, subsequent to the mirror and prior to the collimator, or subsequent to the collimator.

The filter thus creates dark sections in the light field corresponding to leaves (preferably all the leaves) of the collimator. This prevents the incident light from falling on the leaves and removes the ghost images at source. By placing the filter in the head, the line can be very narrow and will be blurred into penumbra at the isocentre. This is therefore a very inexpensive yet effective method of reducing ghosting.

BRIEF DESCRIPTION OF THE DRAWINGS

An embodiment of the present invention will now be described by way of example, with reference to the accompanying figures in which;

FIG. 5 shows alternative placements for the filter.

DETAILED DESCRIPTION OF ILLUSTRATIVE EMBODIMENTS

Figure 1:
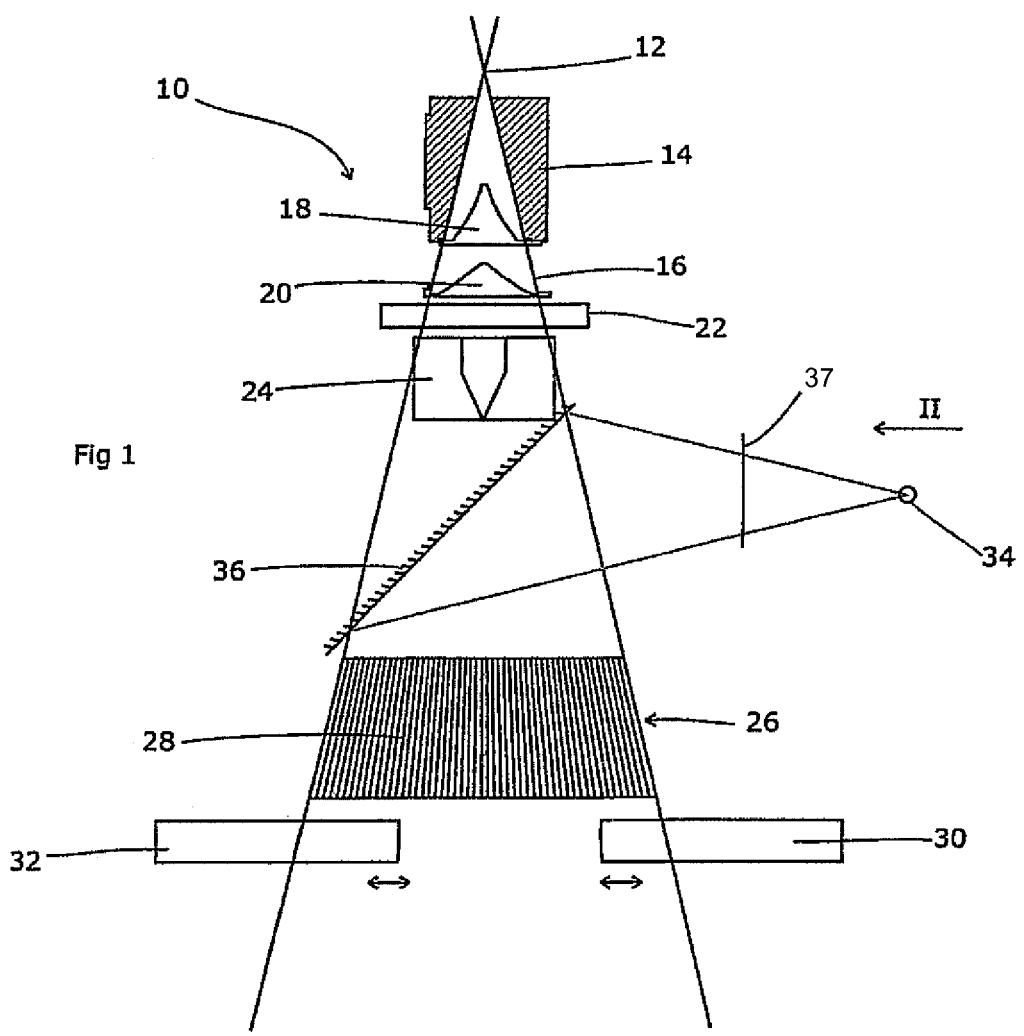
FIG. 1 shows a vertical section through a radiotherapeutic apparatus according to the present invention.

Referring to FIG. 1, a radiotherapeutic apparatus 10 consists of a source of radiation 12 which is then shaped to a cone beam by an aperture collimator 14. The cone-shaped beam of radiation 16 passes through a first filter 18, a second filter 20, both filters being designed to correct the intensity distribution and/or the energy profile of the beam, and then an ion chamber 22 which allows the energy of the beam to be detected and monitored. The beam 16 then passes through a wedge filter 24 which further flattens the intensity distribution across the field of the beam 16, before meeting a multi-leaf collimator 26 composed of a plurality of individual leaves 28.

Each leaf of the multi-leaf collimator 26 can be withdrawn or extended into and out of the path of the beam 16, in a direction transverse to the page as shown in FIG. 1. By extending or withdrawing the individual leaves 28 to a different extent, the beam 16 can be given a specific shape as required by the clinical situation.

After the multi-leaf collimator 26, a pair of block collimators 30, 32, can be extended into and out of the beam in the direction transverse to the direction of the leaf 28 motion, in order to collimate the beam in that axis. Of course, the block collimator 30, 32 could be replaced with a further multi-leaf collimator arranged transverse to the first block collimator 26 in order to provide a more complex shape, or both can be replaced with other arrangements of multi-collimators as for example illustrated in our earlier application No: WO2005/0004987. Further block collimators can also be provided, operating in the same direction as the multi-leaf collimators 26 or any further multi-leaf collimators. These cover the space between extended leaves; multi-leaf collimators are, to a small extent, slightly more leaky than block collimators and therefore if all leaves on that particular bank are extended beyond a particular point, it is possible to extend a block collimator to that particular point so as to provide a reduced background dose.

A light source 34 is provided off to one side of the beam path, and is incident on a mirror 36 that is disposed in the beam path. The mirror 36 and the light source 34 are positioned so that, after reflection, the light field substantially follows the field of the beam of radiation 16. Thus, the light field can replicate the area that will be irradiated by the beam 16. Prior to operation of the radiation source 12, therefore, the light source therefore can be activated so as to verify the positioning of the patient within the beam field, for example by way of a set of cross-hairs, and the operation of the multi-leaf collimator 26 can also be checked visually.

Figure 2:
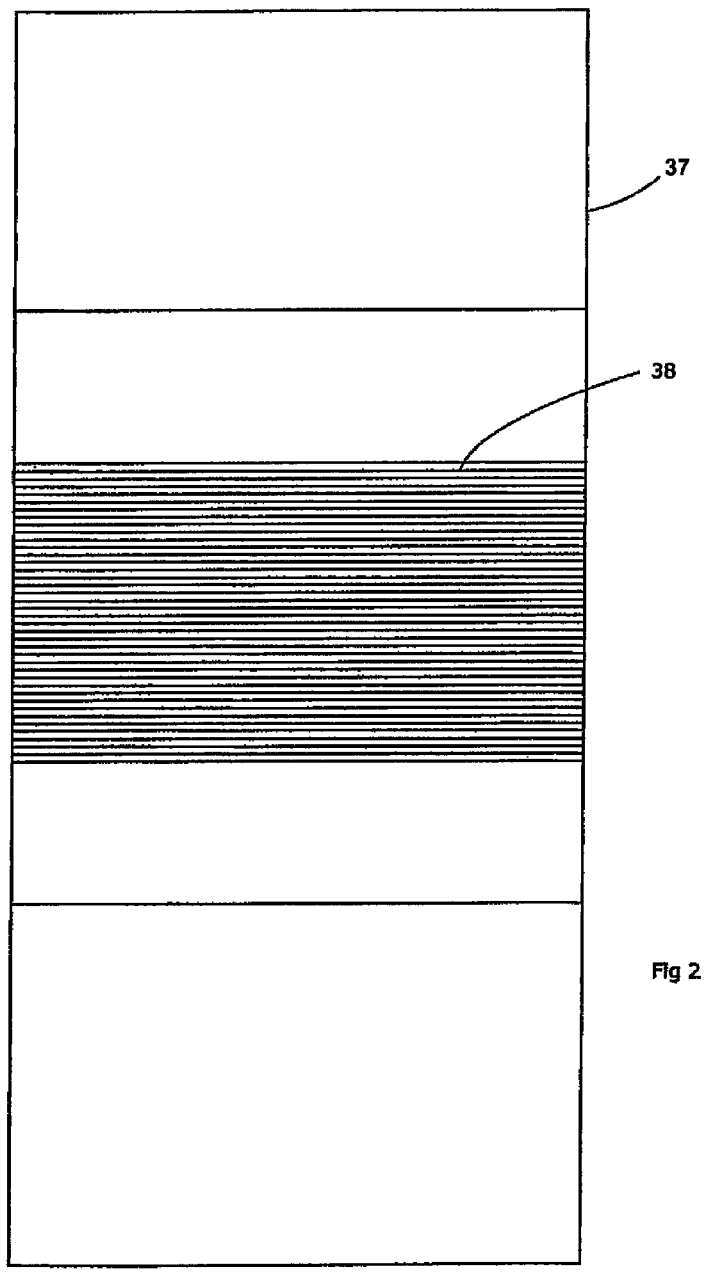
FIG. 2 shows a plan view of the filter fitted to the apparatus of FIG. 1.
Figure 3:
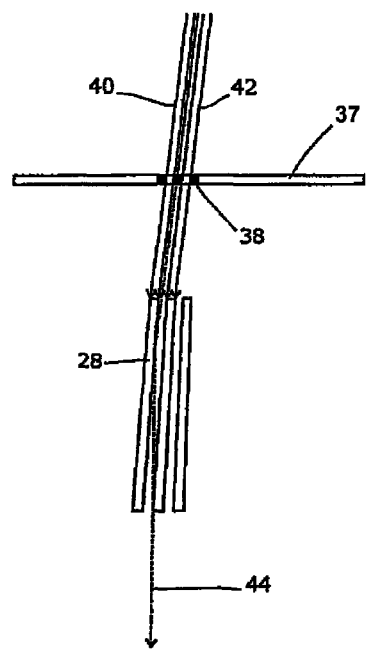
FIG. 3 shows a vertical section through the filter and collimator leaves in more detail.

A filter 37 is placed in the path of the light beam, between the light source 34 and the mirror 36. FIG. 2 shows the filter in the direction of the arrow II on FIG. 1. A plurality of parallel dark lines 38 are provided on the filter 37, and these create a shadow or series of shadows within the light beam. The filter 37 is adjustable as to its fine position, and can therefore be adjusted so that the shadows 38 fall on the sides of the MLC leaves 28 as shown in FIG. 3. According to FIG. 3, light rays 40, 42 are allowed to pass between the dark lines 38 of the filter 37, to fall on the upper edges of the MLC leaves 28. Thus, if the leaf 28 is extended, light that would fall on the leaf sides from which reflections are produced is blocked.

Figure 4:
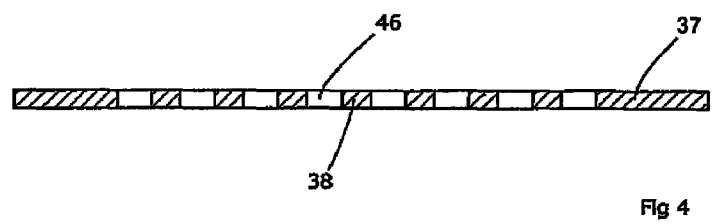
FIG. 4 shows a section through the filter of FIG. 2.

FIG. 4 shows a section through the filter 37. In this embodiment, the filter is formed from a very thin layer of brass, typically approximately 0.5 mm thick. This is etched using a ferric chloride etch, akin to that used for printed circuit boards, in order to form a series of slots 46. In those areas where a slot 46 is not formed, this leaves an area of solid material 38 which defines a dark area of the filter. Various alternative methods could be used for defining the filter 37. For example, the slots 46 could be laser-cut, the filter could be a suitably printed or engraved pattern on a transmissive material such as glass, Perspex or other substantially optically transparent polymeric material, wires could be held under tension in appropriate locations by a suitable frame, suitable masks could be grown chemically, or otherwise.

FIG. 5 shows an alternative apparatus corresponding to that of FIG. 1. Like reference numerals have been used to denote like parts and will not be described further. As can be seen, the filter 38 can be positioned in one of a range of alternative positions. In a first alternative, the filter can be placed very close to the light source, at 48. In this case, the filter is likely to be extremely fine and could be embodied as a suitable diffraction grating in order to create a diffraction pattern equivalent to the image produced by the filter 38. In a further alternative, the filter 38 could be placed between the mirror and the multi-leaf collimator 26, i.e. at 50. Other alternative positions are immediately after the multi-leaf collimator 26 at 52 or after the block collimators 30, 32 at 54.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A radiotherapeutic apparatus comprising a source of therapeutic radiation, a source of visible light arranged to cast a light field corresponding to a beam of radiation, and a multileaf collimator for shaping the beam of radiation, wherein an optical filter comprising an alternating plurality of linear dark and light sections is disposed in the path of a visible light beam, the linear dark sections corresponding to leaves of the collimator and so that the shadows made by the linear dark sections fall on the sides of the leaves to block light from falling on the leaf sides.

2. The radiotherapeutic apparatus according to claim 1 including a mirror to deflect the path of the visible light beam to correspond to that of the radiation beam.

3. The radiotherapeutic apparatus according to claim 2 in which the filter is disposed in the path of the visible light beam prior to the mirror.

4. The radiotherapeutic apparatus according to claim 2 in which the filter is disposed in the path of the visible light beam subsequent to the mirror.

5. The radiotherapeutic apparatus according to claim 1 in which the filter is disposed in the path of the visible light beam prior to the collimator.

6. The radiotherapeutic apparatus according to claim 1 in which the filter is disposed in the path of the visible light beam subsequent to the collimator.

7. The radiotherapeutic apparatus according to claim 4 in which the filter is disposed in the path of the visible light beam prior to the collimator.

8. The radiotherapeutic apparatus according to claim 4 in which the filter is disposed in the path of the visible light beam subsequent to the collimator.

* * * * *